United States Patent
Weaver et al.

(10) Patent No.: US 7,951,121 B2
(45) Date of Patent: *May 31, 2011

(54) PRESSURE ACTUATED VALVE WITH IMPROVED SLIT CONFIGURATION

(75) Inventors: Karla Weaver, Framingham, MA (US); Jim Culhane, Westboro, MA (US)

(73) Assignee: Navilyst Medical, Inc., Marlborough, MA (US)

( * ) Notice: Subject to any disclaimer, the term of this patent is extended or adjusted under 35 U.S.C. 154(b) by 946 days.

This patent is subject to a terminal disclaimer.

(21) Appl. No.: 10/630,885

(22) Filed: Jul. 30, 2003

(65) Prior Publication Data

US 2005/0027261 A1    Feb. 3, 2005

(51) Int. Cl.
*A61M 5/00* (2006.01)
(52) U.S. Cl. ............... 604/247; 604/43; 137/843
(58) Field of Classification Search .......... 604/30, 604/34, 93.01, 264, 27, 173, 167.01–167.04, 604/236–237, 323, 537, 43–45, 244–247; 137/843, 847

See application file for complete search history.

(56) References Cited

U.S. PATENT DOCUMENTS

| | | | | |
|---|---|---|---|---|
| 2,720,881 A | * | 10/1955 | Jones | 604/214 |
| 2,755,060 A | * | 7/1956 | Raymond | 251/342 |
| 3,710,942 A | | 1/1973 | Rosenberg | |
| 3,788,327 A | * | 1/1974 | Donowitz et al. | 604/247 |
| 4,244,379 A | * | 1/1981 | Smith | 600/579 |
| 4,502,502 A | * | 3/1985 | Krug | 137/512.3 |
| 4,524,805 A | * | 6/1985 | Hoffman | 137/846 |
| 4,722,725 A | | 2/1988 | Sawyer et al. | |
| 5,201,722 A | | 4/1993 | Moorehead et al. | |
| 5,324,274 A | * | 6/1994 | Martin | 604/248 |
| 5,395,352 A | | 3/1995 | Penny | |
| 5,453,097 A | * | 9/1995 | Paradis | 604/247 |
| 5,810,789 A | * | 9/1998 | Powers et al. | 604/523 |
| 6,099,505 A | * | 8/2000 | Ryan et al. | 604/167.04 |
| 7,252,652 B2 | * | 8/2007 | Moorehead et al. | 604/247 |
| 7,435,236 B2 | * | 10/2008 | Weaver et al. | 604/6.1 |
| 2004/0102738 A1 | * | 5/2004 | Dikeman et al. | 604/256 |
| 2004/0186444 A1 | * | 9/2004 | Daly et al. | 604/247 |

FOREIGN PATENT DOCUMENTS

| | | |
|---|---|---|
| EP | 0337617 | 10/1989 |
| JP | 04-246370 | 9/1992 |
| JP | 9 038198 | 2/1997 |
| JP | 09038197 A * | 2/1997 |
| JP | 2002/516580 | 6/2002 |

* cited by examiner

*Primary Examiner* — Theodore J Stigell
(74) *Attorney, Agent, or Firm* — Bingham McCutchen LLP (57) ABSTRACT

A valve apparatus for medical applications, comprises a flexible member extending across a lumen through which a flow of materials is to be controlled. The flexible member includes a plurality of movable elements formed on opposite sides of a slit extending through the flexible member. The moveable members are biased so that when a pressure less than a predetermined threshold value is applied to the flexible member, the moveable elements are maintained in a closed position in which no flow is permitted past the flexible member and, when a pressure at least as great as the threshold value is applied to the flexible member, the moveable elements are moved to an open position separated from one another along the slit permitting flow through the lumen.

22 Claims, 4 Drawing Sheets

PRESSURE ACTUATED VALVE WITH IMPROVED SLIT CONFIGURATION

BACKGROUND INFORMATION

Many medical procedures require repeated and prolonged access to a patient's vascular system. For example, during dialysis treatment blood may be removed from the body for external filtering and purification, to make up for the inability of the patient's kidneys to carry out that function. In this process, the patient's venous blood is extracted, processed in a dialysis machine and returned to the patient. The dialysis machine purifies the blood by diffusing harmful compounds through membranes, and may add to the blood therapeutic agents, nutrients etc., as required before returning it to the patient's body. Typically the blood is extracted from a source vein (e.g., the vena cava) through a catheter sutured to the skin with a distal needle of the catheter penetrating the source vein.

It is impractical and dangerous to insert and remove the catheter for each dialysis session. Thus, the needle and catheter are generally implanted semi permanently with a distal portion of the assembly remaining within the patient in contact with the vascular system while a proximal portion of the catheter remains external to the patient's body. The proximal end is sealed after each dialysis session has been completed to prevent blood loss and infections. However, even small amounts of blood oozing into the proximal end of the catheter may be dangerous as thrombi can form therein due to coagulation which thrombi may then be introduced into the patient's vascular system when blood flows from the dialysis machine through the catheter in a later session.

A common method of sealing the catheter after a dialysis session is to shut the catheter with a simple clamp. This method is often unsatisfactory because the repeated application of the clamp may weaken the walls of the catheter due to the stress placed on the walls at a single point. In addition, the pinched area of the catheter may not be completely sealed allowing air to enter the catheter which may coagulate any blood present within the catheter. Alternatively, valves have been used at the opening of the catheter in an attempt to prevent leaking through the catheter when the dialysis machine is disconnected. However, the unreliability of conventional valves has rendered them unsatisfactory for extended use.

SUMMARY OF THE INVENTION

In one aspect the present invention is directed to a valve apparatus for medical applications, comprising a flexible member extending across a lumen through which a flow of materials is to be controlled. The flexible member includes a plurality of movable elements formed on opposite sides of a slit extending through the flexible member. The moveable members are biased so that when a pressure less than a predetermined threshold value is applied to the flexible member, the moveable elements are maintained in a closed position in which no flow is permitted past the flexible member and, when a pressure at least as great as the threshold value is applied to the flexible member, the moveable elements are moved to an open position separated from one another along the slit permitting flow through the lumen.

In a different aspect, the present invention is directed to a dialysis connector comprising a valve housing having a first end connectable to a patient line and a second end mounted to a dialysis line and a flow passage of the housing being connected to the patient line and being operatively connectable to the dialysis line in combination with a valve element mounted within the flow passage of the housing, the valve element including a flexible member extending across the flow passage, the flexible member including a plurality of movable elements formed on opposite sides of a first slit extending through the flexible member, the moveable members being biased so that, when a pressure less than a predetermined threshold value is applied to the flexible member, the moveable elements are maintained in a closed position in which no flow is permitted past the flexible member and, when a pressure at least as great as the threshold value is applied to the flexible member, the moveable elements are moved to an open position separated from one another along the first slit permitting flow through the flow passage.

In yet another aspect, the invention is directed to a flow shutoff device for medical applications comprising a housing attachable to a patient line and a pressure actuated valve mounted within the housing to selectively restrict flow therethrough, wherein movable elements of the valve are biased toward a closed position and are movable to an open position when a pressure applied to the valve exceeds a predetermined threshold value. Flow through the housing is prevented when the movable elements are in the closed position.

DETAILED DESCRIPTION

Semi-permanently placed catheters may be useful for a variety of medical procedures which require repeated access to a patient's vascular system in addition to the dialysis treatments mentioned above. For example, chemotherapy infusions may be repeated several times a week for extended periods of time. For safety reasons, as well as to improve the comfort of the patient, injections of these therapeutic agents may be better carried out with an implantable, semi-permanent vascular access catheter. Many other conditions that require chronic venous supply of therapeutic agents, nutrients, blood products or other fluids to the patient may also benefit from implantable access catheters, to avoid repeated insertion of a needle into the patient's blood vessels. Thus, although the following description focuses on dialysis, those skilled in the art will understand that the invention may be used in conjunction with any of a wide variety of procedures which require long term implantation of catheters within the body.

Examples of such implantable catheters include those manufactured by Vaxcel™, such as the Chronic Dialysis Catheter and the Implantable Vascular Access System. These devices typically are inserted under the patient's skin, and have a distal end which includes a needle used to enter a blood vessel. The devices also have a proximal end extending outside the body for connection with an outside line. These semi-permanent catheters may be sutured to the patient's skin to maintain them in place while the patient goes about his or her normal occupations.

Figure 1:
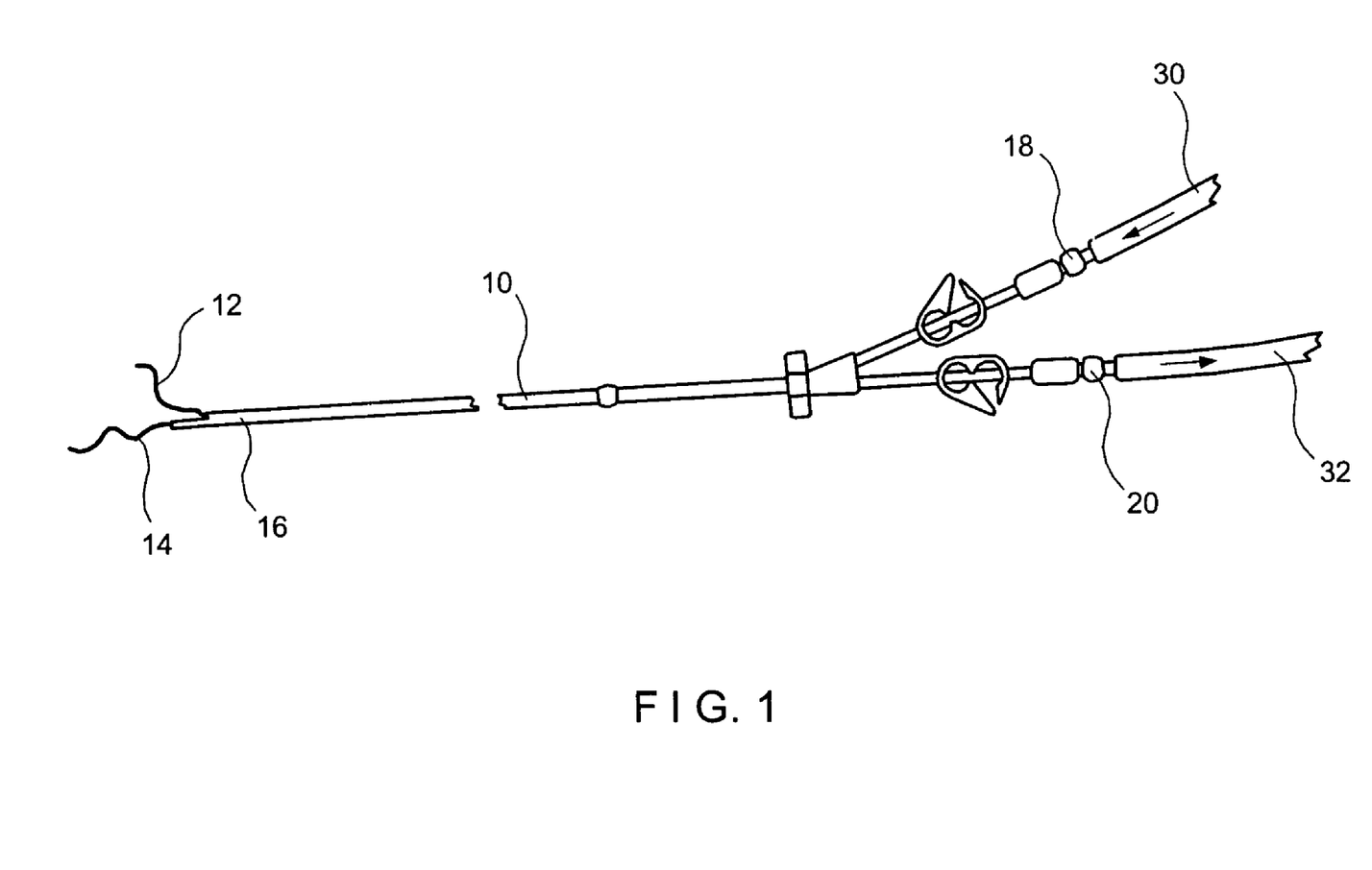
FIG. 1 is a schematic diagram of a vascular access catheter.
Figure 2:
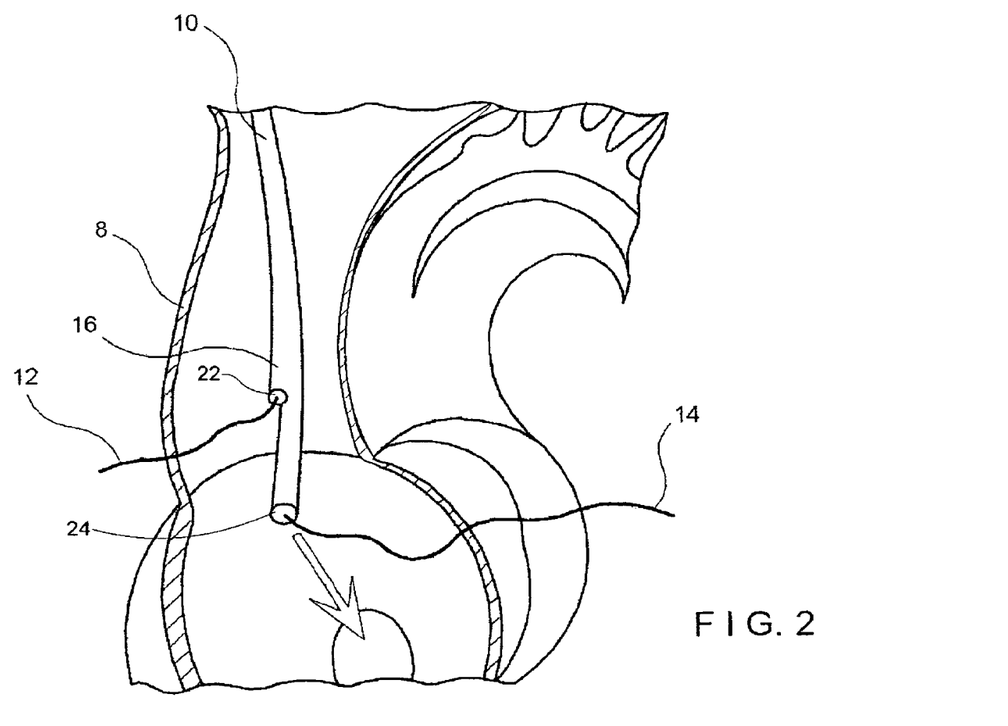
FIG. 2 is a schematic drawing of a vascular access catheter inserted in a patient's vein.

FIGS. 1 and 2 show an exemplary implantable catheter for kidney dialysis. Catheter 10 has a distal end 12 that is insertable under the skin and into the patient's vein, and which remains within the patient's body for the life of the catheter 10. For example, catheter 10 may remain implanted in the patient for two years. As shown more clearly in FIG. 2, distal end 12 fits within a vein 8 (e.g., the vena cava). During dialysis, blood from the patient is removed through a patient line such as catheter 10, and is purified by a dialysis machine (not shown) which is connected to hubs 18 and 20 of catheter 10 by a dialysis line. Catheter 10 in this example includes two lumens 22 and 24 which are used respectively to remove blood from and reintroduce blood to the vessel 8. Lumen 22 terminates at an inflow tip 14 formed at the distal end 12 of the catheter 10 while lumen 24 terminates at an outflow tip 16 formed at the distal end 12. Inflow tip 14 and outflow tip 16 are connected to corresponding inflow and outflow hubs 18, 20, which are accessible outside the body and which may be connected to external lines leading to and from the dialysis machine.

After the dialysis or other procedure has been completed, the catheter 10 is disconnected from the dialysis machine, and is left within the patient fluidly coupled to the patient's vascular system. When not connected to a dialysis machine, the catheter 10 is securely sealed to prevent fluids and gases from crossing into the proximal end of catheter 10 by preventing flow in and out of catheter 10 through hubs 18, 20. As would be understood by those skilled in the art, this sealing prevents the risks associated with infections and thrombi which might be experienced if air or other gas or liquid and/or pathogens were to pass into the catheter 10.

As indicated above, although conventional clamps or clips may be used to seal the catheter 10 between medical sessions, over time the wall of the catheter 10 may be damaged in the area to which the clamp or clip is applied. Sealing clamps or clips may also become dislodged during patient activities, increasing the risk of leaks, infections, etc. Placing a clamp on the catheter 10 also increases the bulk of the distal end of the catheter which is exposed outside the patient's body, and may adversely affect patient comfort.

Therefore, the catheter 10 includes one or more self sealing valves along each of the lumens 22, 24 to seal them when not being used during dialysis and other transfusion or infusion sessions. For example, hubs 18, 20 may be used to house one or more valves each of which is designed to seal the corresponding lumen 22, 24 under certain conditions, and to allow passage of fluids under other conditions. For example, in the case of dialysis treatment, the system of valves may seal the catheter 10 when it is not connected to an operating dialysis machine, and may allow both an outflow of non-purified blood and an inflow of purified blood to the patient when an operating dialysis machine is connected thereto.

Preferably, a valve system for use in such semi-permanent catheters should, when in the open position, allow a flow rate therethrough which is sufficient to allow the procedure to be completed in an acceptably short time. When in the closed position, the valve should completely seal the catheter. That is, if the valve requires excessive force to be opened, the flow rate through the catheter may be reduced to the point where the time required for the procedure is unacceptably extended. In addition, a valve system having moving parts of too great a bulk may also result in larger blockages within the catheter or the hub housing the valve thereby reducing the flow rate through the catheter. The mechanism that moves the valve into the open and closed positions may block the flow through the valve if it protrudes into the flow passage, and thus the size and bulk of the mechanism should preferably be minimized to avoid impeding flow through the open valve.

The portion of the valve that moves to the open position must also completely return to the closed position when the session is completed. For example, a pressure sensitive valve may be used, which opens in response to a pressure driving the flow through the catheter. In the case of a dialysis catheter, the valve or valves may open when a pressure generated by the dialysis machine exceeds a predetermined threshold to allow circulation and purification of the patient's blood. When the dialysis machine is turned off and the pressure in the dialysis line is reduced below the threshold, the valve is completely sealed to prevent further flow from and to the patient. Some pressure is also present in the patient line connecting the valve to the patient's vein as a result of the circulation in the patient's vascular system. Each of the valves must therefore be designed so that it will not respond to such pressure variations introduced by the vascular system and will not open unless a pressure above the threshold is generated externally, for example, by a dialysis machine.

The exemplary embodiments according to the present invention described herein obtain both a secure closure of a semi-permanent catheter implanted in a patient when the catheter is not in use and permit a flow passage that is easily opened to allow a sufficient flow rate when access to the vascular system is necessary.

In many applications, the pressure actuated valve system remains open for the entire length of a therapeutic session, which may last a significant amount of time. For example, in the case of a dialysis session, the valve system may remain open for up to four hours at a time, during sessions carried out up to three times a week. The exemplary embodiments of valves according to the present invention provide a seal to the catheter even after being maintained in the open position for prolonged periods of time.

Figure 3:
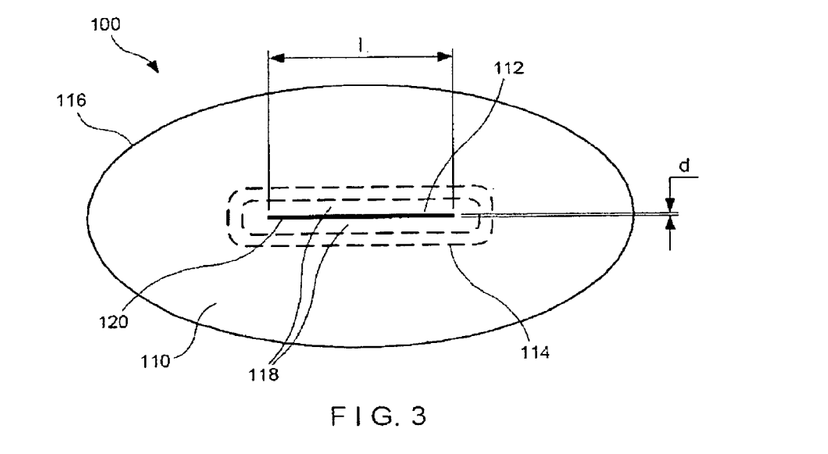
FIG. 3 is a top elevation view of a valve element according to an exemplary embodiment of the present invention.

Specific embodiments of the present invention will be described below with reference to the drawings. FIG. 3 shows a top plan view of an exemplary embodiment of a valve element 100 used to control the flow through a medical tube such as the catheter 10 of FIG. 1. For example, valve element 100 may be located in a flow passage within a valve housing formed in either or both of the hubs 18, 20, through which fluids flow to and from the distal end 12. As will be apparent to those skilled in the art, the valve housing may be placed at any other location along the length of catheter 10 and may be unitary with the catheter 10, or may be formed as a separate component. In addition, it will be apparent that a single valve housing with dual flow passages and one valve 100 within each of the flow passages may be provided instead of two separate valve housings for the hubs 18, 20, respectively, to independently control fluid flow in each direction. Inflow to the patient may take place via one of the dual flow passages of the single hub, and outflow from the patient via the other flow passage.

In the exemplary embodiment shown in FIG. 3, the valve element 100 is formed as a flexible disk 110 having dimensions appropriate to the size of the flow passage within the one of the hubs 18, 20 into which it is to be mounted. The flexible disk 110 may be formed of any sufficiently flexible material, such as a polymeric material. More specifically, the flexible disk 110 may be formed of silicone. The flexible disk 110 may also include a peripheral portion 116 adapted to be connected to an inner surface of the flow passage to seal perimeter of the flow passage around flexible disk 110. The valve element 100 includes a slit 112 which is extends through the entire thickness of the flexible disk 110. The slit 112 separates two movable elements 118 from one another to form an openable portion of the disk 110 which creates a flow passage therethrough when the movable elements 118 are placed in an open position separated from one another. For example, when the edges 120 of the movable elements 118 are moved out of the plane of the flexible disk 110, an opening through the flexible disk 110 is formed along the slit 112. In this exemplary embodiment, the movable elements 118 are formed as resilient flaps substantially constrained in all directions except along the slit 112. Accordingly, the elements 118 are substantially constricted and may only move along the edges 120 to form a relatively small opening.

In one exemplary embodiment the valve element 100 is used in conjunction with dialysis equipment, and movement of movable elements 118 to the open position is prompted by an actuating pressure of a fluid within dialysis lines 30, 32 which may be connected to the hubs 18, 20, respectively, to connect the catheter 10 to a dialysis machine. In particular, an actuating pressure is generated by pumps in the dialysis machine to move the patient's blood between the patient and the filtration equipment. Although the movable elements 118 are formed as flexible flaps, they are formed with a predetermined amount of resilience to allow them to remain in the closed position when not acted upon by the pressure in dialysis lines 30, 32. Specifically, the elements 118 are biased to remain in the closed position abutting one another along edges 120 at all times when they are not acted on by a pressure outside a range of approximately 22 to 44 mmHg. Specifically, as mentioned above, the elements 118 are formed so that the amount of resilience is sufficient to maintain them in the closed position without being forced open by fluid forces generated by natural circulation of the patient's blood. As would be understood by those skilled in the art, the amount of pressure required to open the movable elements 118 is a function of the resilience of the material forming those elements, the size and shape of the slit 112, and the size of the flow passage containing the valve element 100. The details of the geometry of the slit 112 and the movable elements 118 may be selected to obtain the desired characteristics of maximum flow in the open position, and to ensure that valve element 100 seals the flow passage when the pressure is removed.

A stiffening element 114 may be included in valve element 100, to better control the amount of force biasing the movable elements 118 to the closed position. In particular, coupling a stiffening element to an otherwise flexible disk 110 (or forming a stiffening element integrally therewith) provides a valve element 100 including movable elements 118 more resistant to plastic deformation during sessions lasting multiple hours in which the valve element 100 is kept open. An example of a suitable stiffening member is the addition of stiffening ring 114 to the flexible disk 110. The stiffening element 114 may, for example, be formed of a wire or embedded within the valve element 100. Of course, those skilled in the art will understand that the stiffening element 114 may be formed of metal, plastic or any substantially rigid material.

In one exemplary embodiment, the stiffening ring 114 may be embedded within the material of the disk 110, to minimize the bulk of the combination. In different embodiments, stiffening elements may be bonded to one or both sides of the valve element 100, depending on the requirements of the use of the valve element 100. The shape of the stiffening elements used in the valve element 100 may also be modified, depending on the desired characteristics of the force urging the movable elements 118 to the closed position. Alternatively, the stiffening elements may be integrally formed with the disk 110.

As indicated above, the maximum flow that can pass through valve element 100 and the ability to close fully when the actuating pressure is removed are important design parameters for the pressure actuated valves described herein. According to embodiments of the invention, these design parameters may be controlled by properly shaping and sizing the slit or slits 112. Selection of the dimensions of the slit 112 results in movable elements 118 having a desired shape and being constrained along selected edges. In the exemplary embodiment shown in FIG. 3, a linear slit having a width d of approximately 0.002 inches and a length of approximately 0.150 to 0.280 inches is provided in the center of an oval flexible disk 110 extending along a major axis of the disk. The flexible disk 110 could have a thickness of approximately 0.015 to 0.030 inches and could be manufactured from silicone, as a result its surface resistivity rating would be approximately 35 to 70 A. The movable elements 118 used in this configuration are flaps that form an opening by deflecting away from the plane of the disk 110 due to their flexibility, since they are constrained along all sides except along the slit 112. This configuration provides satisfactory performance in a dialysis catheter application, with the catheter having conventional dimensions and providing conventional flow rates. For example, the pressure to which the valve may be subjected during dialysis may be in the range of 200 to 285 mmHg while the pressures applied to the valve by the patient's vascular system are expected to remain below 22 mmHg. Thus, the valve system will preferably be designed to remain sealed when not subjected to a pressure of at least 44 mmHg and, when subjected to the a pressure above that threshold should preferably allow a flow rate of at least 300 ml/min and more preferably at least 350 ml/min without substantially failing to meet these criteria during a life span of one or more years while being subjected to 3 or more uses of up to 4 hours each per week.

The performance characteristics of the valve element 100 can be further tuned by selecting an appropriate length l of the slit 112. By altering this length l, both the maximum flow rate and the opening/closing performance of the valve element 100 will be changed. For example, increasing the length of the slit 112, other parameters being the same, increases a maximum size of the opening through the flexible disk 110, and makes it easier to displace the movable elements 118 to the open position as they are unconstrained along longer edges 120. For the same reason, the movable elements 118 are subjected to a reduced force biasing them toward the closed position when the actuating pressure is removed. Both the width d and the length/of the slit 112 are selected as a tradeoff between ease/size of the opening and the biasing force closing the valve element 100 after use.

Figure 4:
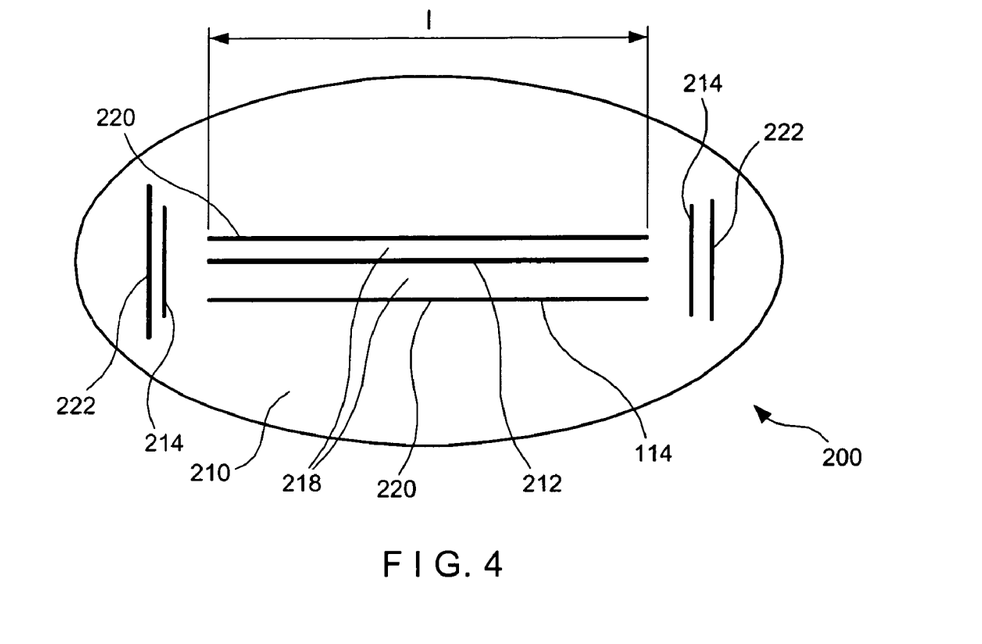
FIG. 4 is a top elevation view of a valve element according to another embodiment of the present invention.

A different exemplary configuration of slits to define the movable elements is shown in FIG. 4. In this embodiment, a flexible disk 210 is provided with slits 212, 214 in a substantially H-shaped configuration that define movable elements 218. The slit 212 is a substantially linear slit aligned with a major dimension of the disk 210, and the slits 214 extend substantially perpendicular to slit 212, disposed near terminating points thereof. This configuration of slits permits the movable elements 218 to more easily move to the open configuration, since each movable element 218 is unconstrained along both the slit 212 and the slits 214. The pressure generated by an external pump, such as a dialysis pump, thus can more easily force the movable elements 218 to the open position. The two additional unconstrained sides of the movable elements 218 also form a larger open area of the flexible disk 210, so that a greater flow rate can pass through the valve element 200.

Additional resilient elements may also be used in the exemplary embodiment shown in FIG. 4 to achieve desired closing characteristics of the valve element 200. For example, a pair of resilient elements 220 may be disposed substantially parallel to the slit 212 on either side thereof. The resilient elements 220 control the deflection and provide a force biasing the movable elements 218 toward the closed position along the axis of the slit 212. Those skilled in the art will understand that additional resilient elements 222 may be used to increase the biasing force and/or to control the deflection of the movable elements 218 along an axis parallel to the slits 214. This exemplary combination of H-configured slits and corresponding H-configured resilient elements results in a high flow, easily opened pressure actuated valve element 200, which is able to completely return to the closed position once the actuating pressure is removed. This configuration also resists plastic deformation that may occur when valve elements are kept in the open position for extended periods of time, and which may prevent the valve from fully closing due to retaining a "memory" of the open position.

Figure 5:
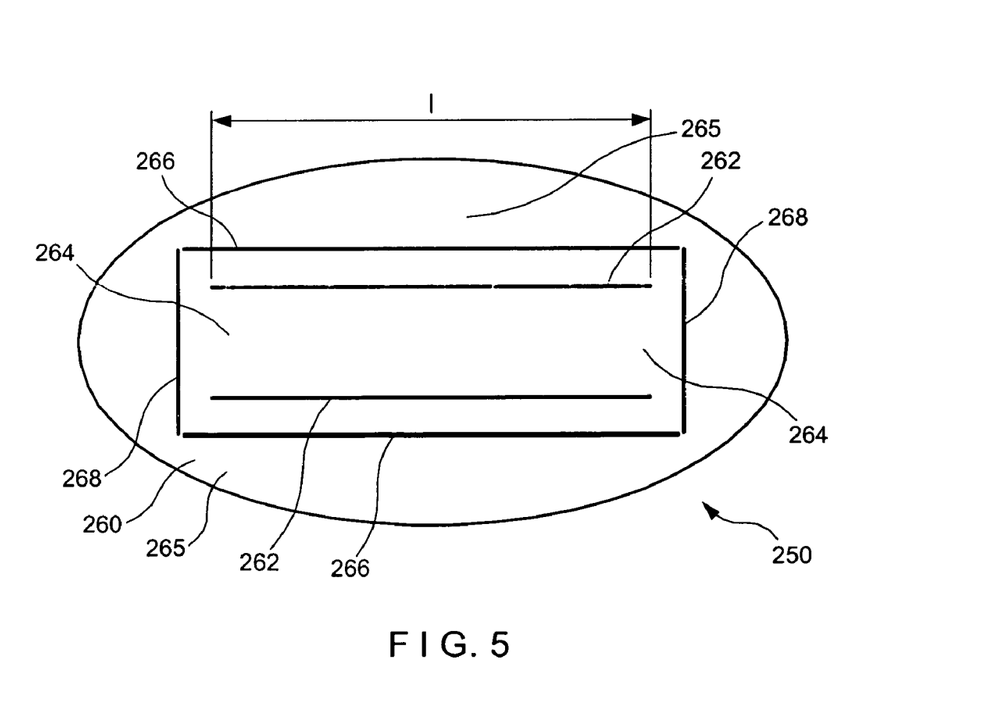
FIG. 5 is a top elevation view of a valve element with double horizontal slits according to an embodiment of the present invention.

Another exemplary embodiment according to the present invention is depicted in FIG. 5. In this embodiment, a double horizontal slit is used to define the movable elements of a valve element 250. More specifically, a pair of substantially parallel slits 262 extends through the flexible disk 260, substantially along a major dimension thereof. In the case of a substantially elliptical flexible disk 260, as shown, the slits 262 are substantially parallel to a major axis of the ellipse. A movable element 264 is thus defined substantially at the center of the flexible disk 260, and is constrained only at ends 265 thereof near termination points of the slits 262.

The greater unconstrained length of the sides of the movable element 264 along the slits 262, enables a large flow area to open as a result of an actuating pressure. For the same reason, a relatively low actuating pressure is needed to open the movable element 264. To ensure a complete closing of valve element 250 when the actuating pressure is removed, for example, resilient elements may be added around the slits 262 to further bias the movable element 264 to the closed position. In the exemplary embodiment shown in FIG. 5, resilient elements 266, 268 are disposed in a substantially rectangular configuration surrounding the slits 262. In this configuration the resilient elements 266, 268 control the deflection of the movable element 264 in directions substantially parallel and perpendicular to the slit orientation and provide a biasing force that closes the movable element 264 when the actuating pressure is removed. The resilient elements 266, 268 may form a complete rectangle, or may be separated at the vertices.

Figure 6:
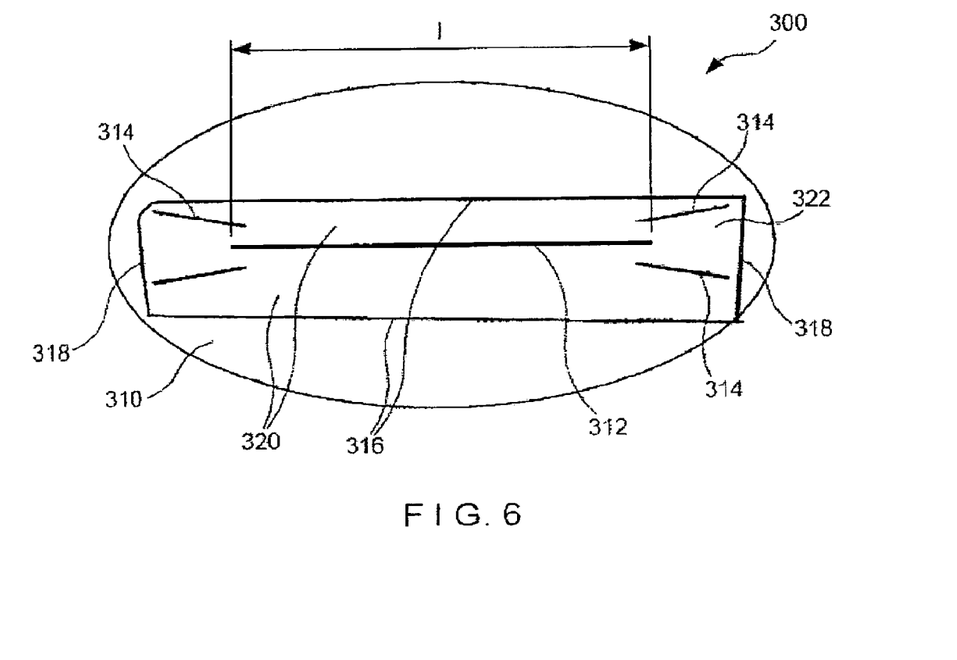
FIG. 6 is a top elevation view of a valve element with Y-configured slits according to an embodiment of the present invention.

FIG. 6 shows yet another embodiment of the pressure actuated valve according to the present invention. In this exemplary embodiment, a linear slit is combined with a pair of Y-configured slits to provide a larger flow area when the valve element is placed in the open position by an actuating pressure thereagainst. As shown in the drawing, the valve element 300 is formed as a flexible disk 310 which, in this example, has a substantially elliptical shape. It will be apparent to those skilled in the art that different shapes of the flexible disk 310 may be used, depending on the shape and dimensions of the housing in which the valve element 300 is placed. A linear slit 312 is formed in the flexible disk 310, for example along a major dimension thereof, and is complemented by two pairs of slits 314. A first pair of the slits 314 is disposed at a first end of the slit 312 with a second one of the pairs of slits 314 being formed at the second end of the slit 312. The slits 314 are formed at an angle with the slit 312, so that, at each end of the slit 312, a substantially Y-shaped configuration of slits is formed.

In the exemplary embodiment shown, the slits 312 and 314 do not touch one another so that the movable elements 320 are continuous with portions 322 of the flexible disk 320. In different embodiments, the slits 312 and 314 may intersect with one another, breaking the flexible disk 320 into additional distinct moving elements. In the exemplary embodiment shown, the movable elements 320 are unconstrained along the slits 312, 314, but are constrained in the region between the slits by being continuous with the portions 322 of the flexible disk 320. The addition of the Y-configured slits permits the movable elements 320 to open to a greater extent under an actuating pressure, while retaining a biasing force sufficient to close the opening when the actuating pressure is removed. To further bias the movable elements 320 toward the closed position, resilient elements 316, 318 may be added. As discussed in the context of previous embodiments, the resilient elements 316, 318 may be disposed in a substantially rectangular pattern around the slits 312, 314 to control the deflection and closure of the movable elements 320 in two perpendicular directions. The resilient elements 316, 318 may form a completely rectangular enclosure as shown in FIG. 6, or may have open vertices, as shown in previous embodiments. As would be understood by those skilled in the art, the relative size and orientation of the slits 312, 314 may be selected to give desired flow and closing properties, for a given flexible disk 320.

Figure 7:
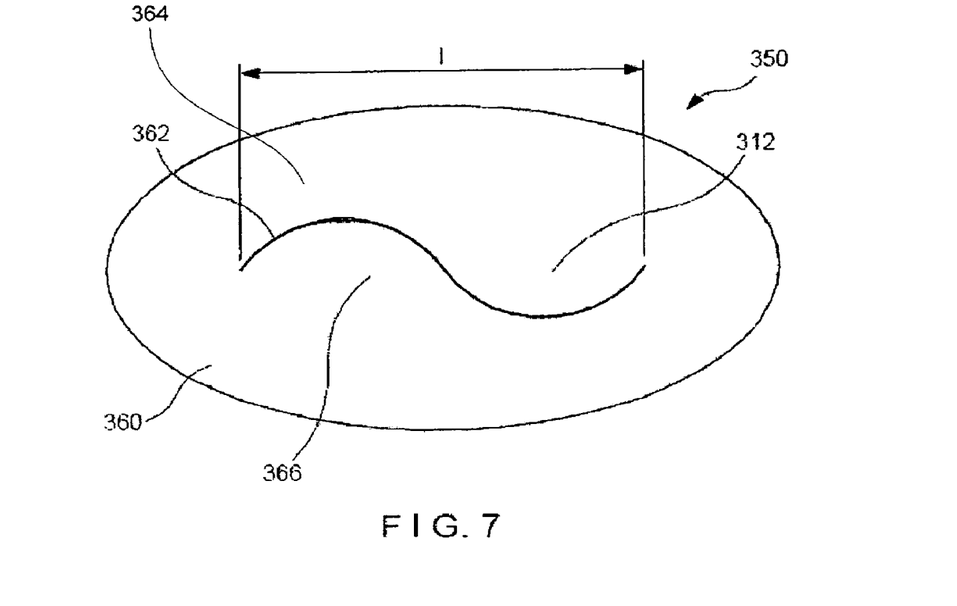
FIG. 7 is a top elevation view of a valve element with a curved slit according to an embodiment of the present invention.

A further exemplary embodiment of the invention is depicted in FIG. 7. In this example, the valve element 350 comprises a flexible disk 360 having a slit 362 extending therethrough. The slit 362 is not a linear slit, but instead is curved about a principal axis of the flexible disk 360. In the example shown in FIG. 7, the slit 362 follows a generally sinusoidal path. However other curved paths may be used with similar effect. The slit 362 defines two movable elements 364, 366 which are complementary to each other on opposite sides of the slit 362. A benefit of this configuration is that, for a given length/of the slit 362, a larger opening area of the valve element 350 may be obtained. Since the unconstrained edges of the movable elements 364, 366 are longer due to their curved shape, a given actuating pressure is able to displace a larger portion of the movable elements 364, 366 to the open position. This allows for a larger flow area through the valve element 350.

As was the case in other exemplary embodiments of the invention, the resilience of the movable elements 364, 366 is controlled to ensure the valve fully closes once the actuating pressure is removed, and is not subject to "memory" effects after being open for extended periods of time. Accordingly, the resilience of the material forming the movable elements 364, 366 can be controlled, and additional resilient elements may be incorporated in the flexible disk 360, as described above with respect to other embodiments.

The present invention has been described with reference to specific exemplary embodiments. Those skilled in the art will understand that changes may be made in details, particularly in matters of shape, size, material and arrangement of parts. For example, different flexible disks may be used to form the pressure sensitive valve, and may have different dimensions than those shown. Furthermore, as would be understood by those of skill in the art, any of the various features of the different embodiments described may be combined in any manner to take advantage of their various properties. Accordingly, various modifications and changes may be made to the embodiments without departing from the broadest scope of the invention as set forth in the claims that follow. The specifications and drawings are, therefore, to be regarded in an illustrative rather than a restrictive sense.

What is claimed is:

1. A valve apparatus for dialysis applications, comprising a first flexible disk extending across a first lumen through which a flow of materials is to be controlled, the first flexible disk including a plurality of first movable elements formed on opposite sides of at least one first slit extending through the first flexible disk, wherein a size and configuration of the first slit is selected to provide desired opening and closing characteristics of the moveable elements, the first moveable element being biased so that, when a pressure less than a predetermined threshold value is applied to the first flexible disk, the first moveable elements are maintained in a closed position in which no flow is permitted past the first flexible disk and, when a pressure at least as great as the threshold value is applied to a planar face of the first flexible disk, the first moveable elements are moved to an open position separated from one another along the at least one first slit permitting flow through the first lumen, the first flexible disk further comprising at least one biasing member coupled thereto adjacent the first slit to increase a biasing force urging the first movable elements toward the closed position, the apparatus further comprising a second lumen with a second flexible disk extending there across, the second flexible disk including a plurality of second movable elements formed on opposite sides of at least one second slit extending through the second flexible disk, the second moveable members being biased so that, when a pressure less than a predetermined threshold value is applied to the second flexible disk, the second moveable elements are maintained in a closed position in which no flow is permitted past the second flexible disk and,
when a pressure at least as great as the threshold value is applied to the second flexible disk, the second moveable elements are moved to an open position separated from one another along the at least one second slit permitting flow through the second lumen.

2. The valve apparatus according to claim 1, wherein the first movable elements are biased toward the closed position by the resilience of the material of the first flexible disk.

3. The valve apparatus according to claim 2, wherein the at least one first slit is substantially linear.

4. The valve apparatus according to claim 3, wherein the substantially linear first slit is substantially parallel to a major axis of the first flexible disk.

5. The valve apparatus according to claim 3, wherein the first flexible disk further includes a pair of additional slits, each of the additional slits intersecting a corresponding end of the first slit.

6. The valve apparatus according to claim 1, further comprising a first housing coupled to a catheter which, when in an operative position, extends into a patient's body to facilitate fluid exchange, the first housing being selectively coupleable to a first external line for fluid transfer between the patient and external devices, wherein the first lumen extends through the first housing.

7. The valve apparatus according to claim 6, further comprising a second housing coupled to the catheter, wherein the first lumen extends through the catheter and wherein the second lumen extends through the second housing and the catheter, the second housing being selectively coupleable to a second external line for fluid transfer between the patient and external devices, and wherein the second flexible disk is within the second housing.

8. The valve apparatus according to claim 6, wherein the first housing is integrally formed with the catheter.

9. The valve apparatus according to claim 6, wherein the catheter includes a tissue penetrating distal end for insertion into a lumen of a vascular organ of the patient and wherein the first flexible disk is constructed so that naturally occurring pressures applied thereto by the patient's vascular system are below the threshold value and a pressure applied to the first flexible disk by an external pump is above the threshold value.

10. The valve apparatus according to claim 1, wherein the lumen is a lumen of a dialysis catheter and wherein the threshold value is set so that movable elements move to the open position in response to pressure generated by a dialysis pump connected to the first housing.

11. The valve apparatus according to claim 1, wherein the at least one biasing member is positioned substantially parallel to the first slit.

12. The valve apparatus according to claim 1, wherein the first flexible disk is formed of silicone.

13. The valve apparatus according to claim 1, wherein the first flexible disk is permanently sealed around an entire perimeter of the first lumen.

14. A dialysis connector comprising:
a valve housing having a first end connectable to a patient line and a second end mounted to a dialysis line;
a flow passage of the housing being connected to the patient line and being operatively connectable to the dialysis line;
a valve element mounted within the flow passage of the housing, the valve element including a flexible disk extending across the flow passage, the flexible disk including a plurality of movable elements formed on opposite sides of a first slit extending through the flexible disk, wherein a size and configuration of the first slit is selected to provide desired opening and closing characteristics of the moveable elements, the moveable members being biased so that, when a pressure less than a predetermined threshold value is applied to a planar face of the flexible disk, the moveable elements are maintained in a closed position in which no flow is permitted past the flexible disk and, when a pressure at least as great as the threshold value is applied to the flexible disk, the moveable elements are moved to an open position separated from one another along the first slit permitting flow through the flow passage, the valve element further comprising biasing elements coupled to the flexible disk adjacent to the first slit to urge the moveable elements toward the closed position.

15. The connector according to claim 14, wherein the first slit is substantially linear and is disposed substantially centrally on the flexible member.

16. The connector according to claim 14, further comprising a plurality of second slits disposed at end points of the first slit.

17. The connector according to claim 16, wherein the second slits are substantially perpendicular to the linear slit.

18. The connector according to claim 16, wherein each of the second slits extends at an angle to the first slit.

19. The connector according to claim 14, wherein the first slit comprises a pair of substantially parallel linear slits.

20. The connector according to claim 14, wherein the movable elements are unconstrained along the first slit.

21. The connector according to claim 14, wherein a first one of the biasing elements is parallel to the first slit and a second one of the biasing elements is perpendicular to the first slit.

22. A flow shutoff device for dialysis applications, comprising:
   a housing attachable to a patient line; and
   a pressure actuated valve mounted within the housing to selectively restrict flow therethrough, the valve comprising a flexible disk including a plurality of movable elements separated by a slit extending through the disk, wherein a size and configuration of the slit is selected to provide desired opening and closing characteristics of the moveable elements, the movable elements being biased toward a closed position and being movable to an open position when a pressure applied to a planar face of the valve exceeds a predetermined threshold value, wherein flow through the housing is prevented when the movable elements are in the closed position, the pressure actuated valve further comprising at least one biasing member coupled thereto to increase a biasing force urging the movable elements toward the closed position.

* * * * *